United States Patent
Zica et al.

(10) Patent No.: US 8,251,980 B2
(45) Date of Patent: Aug. 28, 2012

(54) VISCOUS FLUID EXTRACTION

(75) Inventors: Michael A. Zica, Costa Mesa, CA (US);
Matthew E. Bazydlo, Costa Mesa, CA (US); Steven T. Charles, Memphis, TN (US)

(73) Assignee: Alcon Research, Ltd., Fort Worth, TX (US)

( * ) Notice: Subject to any disclaimer, the term of this patent is extended or adjusted under 35 U.S.C. 154(b) by 263 days.

(21) Appl. No.: 12/749,842

(22) Filed: Mar. 30, 2010

(65) Prior Publication Data
US 2011/0245787 A1   Oct. 6, 2011

(51) Int. Cl.
*A61M 27/00* (2006.01)

(52) U.S. Cl. .......... 604/541; 604/319; 604/19; 604/521; 604/35; 604/28

(58) Field of Classification Search .................. 604/319, 604/541
See application file for complete search history.

(56) References Cited

U.S. PATENT DOCUMENTS

| | | | | |
|---|---|---|---|---|
| 3,439,675 | A | * | 4/1969 | Cohen .......................... 604/192 |
| 5,328,481 | A | * | 7/1994 | Wang ............................ 604/506 |
| 5,336,175 | A | * | 8/1994 | Mames .......................... 604/521 |
| 5,336,487 | A | * | 8/1994 | Refojo et al. ............. 424/78.04 |
| 5,501,676 | A | * | 3/1996 | Niedospial et al. ........... 604/534 |
| 5,743,886 | A | * | 4/1998 | Lynn et al. .................... 604/191 |
| 6,135,984 | A | * | 10/2000 | Dishler .......................... 604/264 |
| 6,282,442 | B1 | * | 8/2001 | DeStefano et al. ............. 604/21 |
| 6,290,690 | B1 | * | 9/2001 | Huculak et al. ............... 604/521 |
| 7,141,048 | B1 | * | 11/2006 | Charles ............................. 606/4 |
| 7,285,107 | B1 | * | 10/2007 | Charles .......................... 604/35 |
| 7,871,399 | B2 | * | 1/2011 | Dacquay et al. .............. 604/291 |
| 2004/0039253 | A1 | * | 2/2004 | Peyman et al. ................ 600/201 |
| 2004/0073231 | A1 | * | 4/2004 | Juan et al. ...................... 606/108 |
| 2004/0122367 | A1 | * | 6/2004 | Sculati .......................... 604/140 |
| 2007/0270744 | A1 | * | 11/2007 | Dacquay et al. .............. 604/114 |
| 2007/0293820 | A1 | * | 12/2007 | Dacquay et al. .............. 604/113 |

OTHER PUBLICATIONS

Stappler et al., "A guide to the removal of heavy silicone oil." (Jun. 2008), Br. J. Opthalmol. V. 92, pp. 844-847.*
Kampik et al., "Siicone Oil Removal Strategies." (Jun. 2000) Seminars Opthalmol. vol. 15 pp. 88-91.*
Hutton et al., "The Effects of Silicone Oil Removal." ARCH Opthalmol. (Jun. 1994) V. 112 pp. 778-785.*
McCabe et al., "Vitrectomy", Chapter 56, Duane's Opthalmology, CD-ROM, 2006 Addition (2006), Lippincott Williams & Wilkins, N.Y.*
Alcon® "CONSTELLATION® VFC Pak", Vitreoretinal Product Catalog, 2008, 2 pgs.

* cited by examiner

*Primary Examiner* — Tatyana Zalukaeva
*Assistant Examiner* — Guy K Townsend
(74) *Attorney, Agent, or Firm* — W. David Lee

(57) ABSTRACT

An extraction sleeve assembly for use in extracting a viscous fluid from the posterior segment of an eye during vitreoretinal surgery is disclosed. The extraction sleeve assembly includes a luer lock fitting and a flexible, tubular extraction sleeve. The extraction sleeve assembly facilitates a shorter extraction time for the viscous fluid.

6 Claims, 2 Drawing Sheets

VISCOUS FLUID EXTRACTION

FIELD OF THE INVENTION

The present invention generally pertains to vitreoretinal surgery and more particularly to consumables for helping to perform fluid exchanges typically used in such surgeries.

DESCRIPTION OF THE RELATED ART

In a healthy human eye, the retina is physically attached to the choroid in a generally circumferential manner behind the pars plana. The vitreous humor, a transparent jelly-like material that fills the posterior segment of the eye, helps to cause the remainder of the retina to lie against, but not physically attach, to the choroid.

Sometimes a portion of the retina becomes detached from the choroid. Other times a portion of the retina may tear, allowing vitreous humor, and sometimes aqueous humor, to flow between the retina and the choroid, creating a build up of subretinal fluid. Both of these conditions result in a loss of vision.

To surgically repair these conditions, a surgeon typically inserts several trocar cannula into the posterior segment of the eye via scleratomies (an incision through the sclera at the pars plana). The surgeon typically inserts a vitrectomy probe into a first trocar cannula, a fiber optic light source into a second trocar cannula, and an infusion cannula into a third trocar cannula. While viewing the posterior segment under a microscope and with the aid of the fiber optic light source, the surgeon cuts and aspirates away vitreous using the vitrectomy probe to gain access to the retinal detachment or tear. The surgeon uses the vitrectomy probe, scissors, a pick, and/or forceps to remove any membrane that has contributed to the retinal detachment or tear and to cause the detached or torn portion of the retina to flatten against the choroid in the proper location. During this portion of the surgery, a saline solution is typically infused into the eye via the infusion cannula to maintain the appropriate intraocular pressure. Once the detached or torn portion of the retina is properly located, the surgeon uses a diathermy probe or a laser to fuse portions of the detached retina in place.

Since a retinal tear or detachment takes a period of weeks to re-attach after the above-described surgical procedure, a retinal tamponading fluid is injected into the posterior segment of the eye to keep the detached or torn portion of the retina properly flatten against the choroid. This retinal tamponade is often a viscous fluid, such as silicone oil. Silicone oil must also be extracted from the eye after the retina re-attaches because it emulsifies and causes vision problems. Such extraction is typically accomplished via syringe having a viscous fluid control cannula on its distal end. The viscous fluid control cannula are typically provided in 20 gauge, 23 gauge, or 25 gauge sizes. The viscous fluid control cannula is inserted into a trocar cannula in the posterior segment of the eye.

Due to the viscosity of silicone oil and the small internal diameters of the viscous fluid control cannula, it often takes a surgeon approximately four minutes to extract the silicone oil from the posterior segment of the eye using, for example, a 25 gauge viscous fluid control cannula, 1000 centistoke silicone oil, and a vacuum of 600 mm Hg. An extraction time of approximately 1.9 minutes is required for a 23 gauge viscous fluid control cannula, 1000 centistoke silicone oil, and a vacuum of 600 mm Hg. A need exists in vitreoretinal surgery for a shorter extraction time for silicone oil, which in turn would result in shorter surgery time, decreased surgeon fatigue, reduced eye trauma, and shorter patient healing times.

SUMMARY OF THE INVENTION

The present invention is an extraction sleeve assembly for use in extracting a viscous fluid from the posterior segment of an eye during vitreoretinal surgery. The extraction sleeve assembly generally includes a luer lock fitting and a flexible, tubular extractive sleeve. The luer lock fitting has a proximal end for fluidly coupling to a distal end of a syringe, a distal male fitting, and an internal bore. The extraction sleeve is friction fit over the distal male fitting so as to create a fluid tight seal between the distal male fitting and an interior surface of the extraction sleeve, and so that a portion of the extraction sleeve having a length suitable to receive a hub of a trocar cannula extends from a distal end of the distal male fitting.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1-4 of the drawings, like numerals being used for like and corresponding parts of the various drawings.

Figure 1:
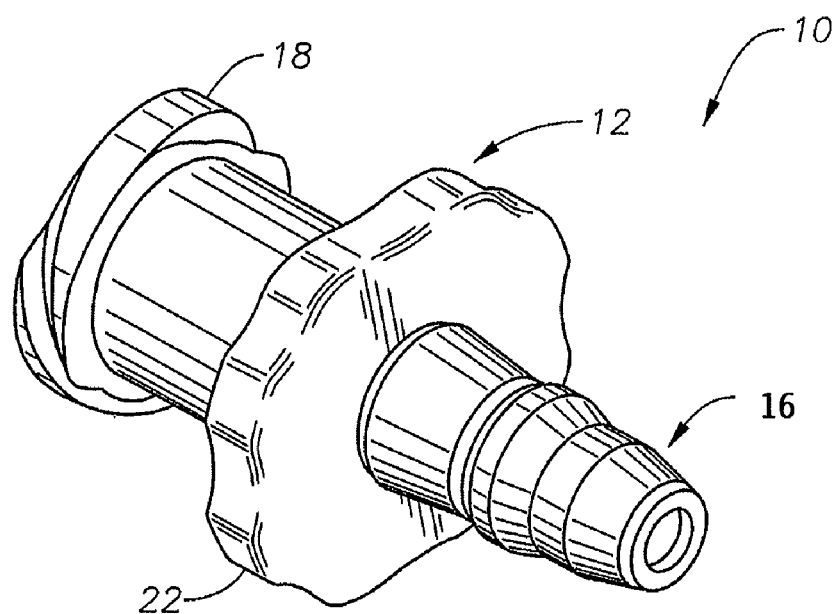
FIG. 1 is a perspective view of an extraction sleeve assembly according to a preferred embodiment of the present invention.
Figure 2:
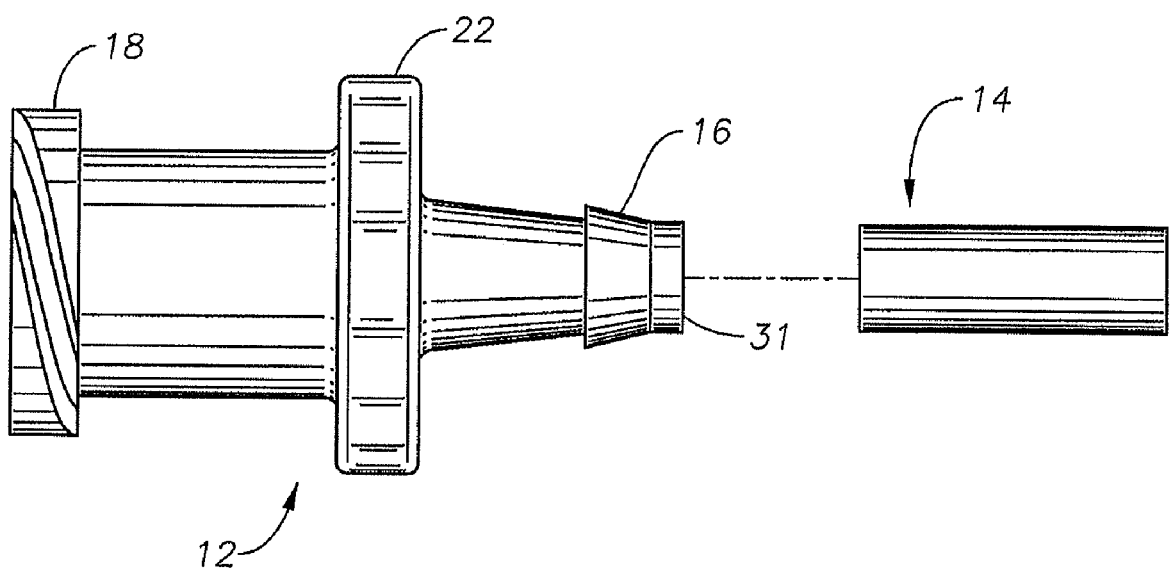
FIG. 2 is a side, exploded view of the extraction sleeve assembly of FIG. 1.
Figure 3:
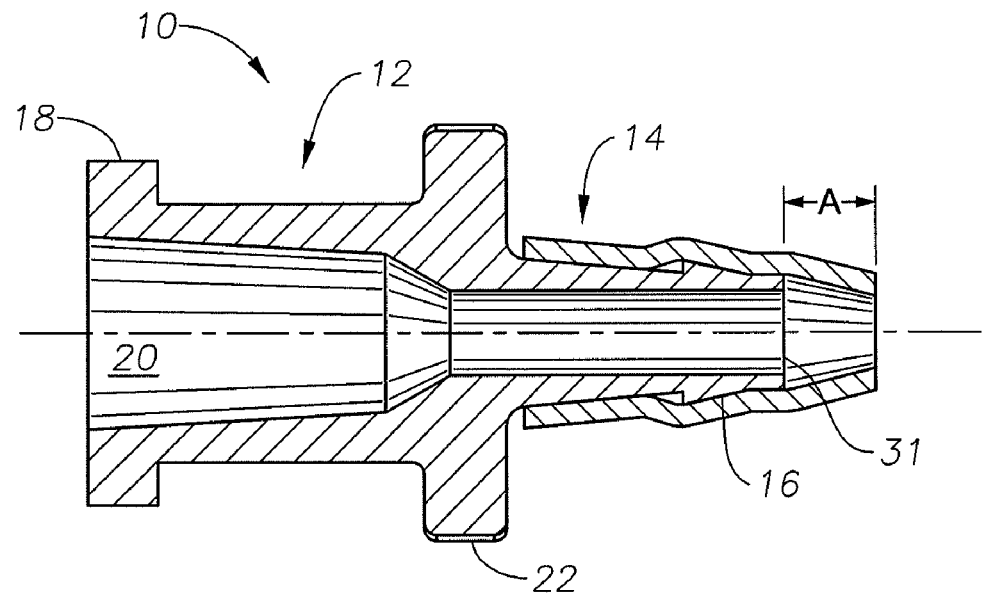
FIG. 3 is side, sectional view of extraction sleeve assembly of FIG. 1.
Figure 4:
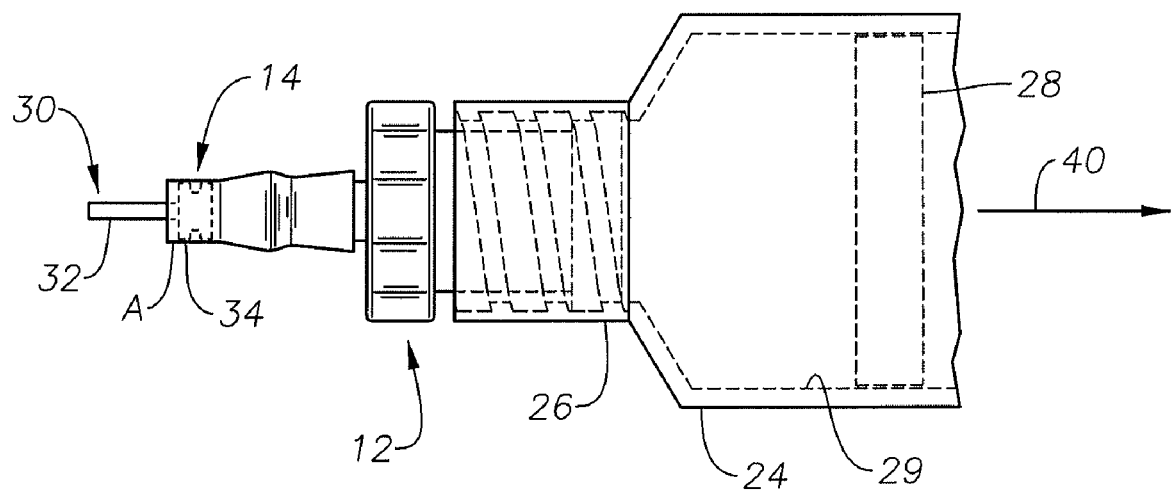
FIG. 4 is side, fragmentary view of the extraction sleeve assembly of FIG. 1 operably coupled to a trocar cannula on a distal end and a syringe on a proximal end.

Extraction sleeve assembly 10 of the present invention generally includes a luer lock fitting 12 and an extraction sleeve 14. Luer lock fitting 12 preferably has a male fitting 16, a threaded collar 18, an internal bore 20, and a grasping portion 22. As shown in FIG. 4, a user may fluidly couple extraction sleeve assembly 10 onto a syringe 24 by disposing threaded collar 18 into threaded distal end 26 of syringe 24 and rotating grasping portion 22. Syringe 24 has a piston 28 that is fluidly sealed and slidably coupled to an internal bore 29. Extraction sleeve 14 is preferably a piece of flexible plastic tubing having a length of about 0.35 inches, an internal diameter of about 0.062 inches, and an external diameter of about 0.081 inches. Extraction sleeve 14 is preferably silicone tubing. As shown best in FIGS. 2 and 3, extraction sleeve 14 is preferably friction fit over male fitting 16 of luer locking fitting 12 so that a portion "A" of extraction sleeve 14 extends from a distal end 31 of male fitting 16. A fluid tight seal is created between male fitting 16 and an interior surface of extraction sleeve 14. Portion "A" preferably has a length of about 0.08 inches. Portion A is for fluidly coupling to a trocar cannula 30, as is shown in FIG. 4. Trocar cannula 30 generally includes a cannula portion 32 surrounded by a proximal hub 34, as is conventional.

Before a surgeon performs a vitreoretinal surgery, a scrub nurse preferably fluidly couples luer lock fitting 12 to syringe 24. The scrub nurse places piston 28 into internal bore 29 of syringe 24 and uses a push rod (not shown) to slide piston 28 toward distal end 26 of syringe 24. The nurse fluidly couples a vacuum source 40 to a proximal end of syringe 24. During the vitreoretinal surgery, a surgeon inserts several trocar cannula 30 into scleratomies, as is described hereinabove. During the later stages of the surgery, the surgeon must extract the viscous fluid retinal tamponade, such as silicone oil, that was injected into the posterior segment of the eye. To perform such extraction, the surgeon first slides portion A of extraction sleeve 14 over the exterior surface of hub 34 of trocar cannula 30. The surgeon then activates vacuum source 40. Vacuum source 40 fluidly couples hub 34 within portion A of extraction sleeve 14, and a fluid tight seal is created between an exterior surface of hub 34 and an interior surface of portion A. Silicone oil begins to flow through cannula portion 32 of trocar cannula 30, internal bore 20 of luer lock fitting 12, and into internal bore 29 of syringe 24. As silicone oil is drawn into syringe 24, piston 28 moves toward the proximal end of the syringe. A surgeon infuses an intraocular irrigating solution into the posterior segment of the eye using an infusion cannula (not shown) inserted into a second trocar cannula 30 while extracting the silicone oil so as to maintain the appropriate intraocular pressure of the eye. When all the silicone oil has been extracted, the surgeon deactivates vacuum source 40 and slides portion A of extraction sleeve 14 off hub 34. The surgeon may then complete the vitreoretinal surgery, as is conventional.

Extraction sleeve assembly 10 allows a surgeon to avoid both the attachment of a viscous fluid control cannula to syringe 24 and the insertion of the viscous fluid control cannula into cannula portion 32 of trocar cannula 30 through hub 34, as is conventional. Since cannula portion 32 of the trocar cannula has a larger internal diameter than the viscous fluid control cannula, and because flow resistance is inversely proportional to the fourth power of the radius of a cannula, extraction sleeve 14 greatly increases the effective flow radius and results in a substantially higher extraction rate for silicone oil. For example, using extraction sleeve assembly 10 with a 23 gauge trocar cannula 30 results in about a 43 percent increase in extraction flow rate, and about a 30 percent decrease in extraction time, over a 23 gauge viscous fluid control cannula for 1000 centistoke silicone oil and a vacuum source 40 set to a vacuum level of 600 mg Hg. As another example, using extraction sleeve assembly 10 with a 25 gauge trocar cannula 30 results in about a 45 percent increase in extraction flow rate, and about a 31 percent decrease in extraction time, over a 25 gauge viscous fluid control cannula for 1000 centistoke silicone oil and a vacuum source 40 set to a vacuum level of 600 mg Hg.

From the above, it may be appreciated that the present invention provides a shorter extraction time for silicone oil during vitreoretinal surgery, which in turn results in shorter surgery time, decreased surgeon fatigue, reduced eye trauma, and shorter patient healing times.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of extracting a viscous fluid from a posterior segment of an eye during vitreoretinal surgery, comprising the steps of:

disposing a trocar cannula in a posterior segment of an eye, said trocar cannula having a distal cannula portion for extension into said posterior segment and a proximal hub for contacting a sclera of said eye;

providing an extraction sleeve assembly, said extraction sleeve assembly comprising:

a luer lock fitting having a proximal end for fluidly coupling to a distal end of a syringe, a distal male fitting, and an internal bore; and a flexible, tubular extraction sleeve friction fit over said distal male fitting so as to create a fluid tight seal between said distal male fitting and an interior surface of said extraction sleeve, and so that a portion of said extraction sleeve having a length suitable to receive said hub of said trocar cannula extends from a distal end of said distal male fitting;

fluidly coupling said luer lock fitting to said distal end of said syringe;

fluidly coupling a proximal end of said syringe to a vacuum source;

disposing said portion of said extraction sleeve over said hub of said trocar cannula;

activating said vacuum source; and extracting a viscous fluid from said posterior segment through said trocar cannula, said extraction sleeve assembly, and into said syringe.

2. The method of claim 1 wherein said viscous fluid is a retinal tamponading fluid.

3. The method of claim 2 wherein said retinal tamponading fluid is silicone oil.

4. The method of claim 1 wherein said step of activating said vacuum source creates a fluid tight seal between an exterior surface of said hub and an interior surface of said portion of said extraction sleeve.

5. The method of claim 1 wherein wherein said extraction sleeve is made of silicone tubing.

6. The method of claim 1 wherein said portion has a length of about 0.08 inches and an internal diameter of about 0.062 inches at a distal end of said portion.

* * * * *